US 6,709,725 B1

(12) United States Patent
Lai et al.

(10) Patent No.: US 6,709,725 B1
(45) Date of Patent: Mar. 23, 2004

(54) ELASOMERIC ARTICLE

(75) Inventors: Hee-Meng Lai, Melaka (MY); Paul Cacioli, Canton, OH (US); Soo-Hwa Kwan, Melaka (MY); Soon-Kiang Ng, Melaka (MY); Adeli Kassim, Melaka (MY); Wan Nasaruddin, Melaka (MY); Yunus Husin, Melaka (MY); Yong-Poon Tan, Melaka (MY)

(73) Assignee: Ansell Medical Sdn, Bhd., Melaka (MY)

( * ) Notice: Subject to any disclaimer, the term of this patent is extended or adjusted under 35 U.S.C. 154(b) by 0 days.

(21) Appl. No.: 09/515,422

(22) Filed: Feb. 29, 2000

(51) Int. Cl.⁷ .................... A41D 19/00; B32B 7/02; B32B 1/08
(52) U.S. Cl. .................... 428/36.8; 428/216; 2/168
(58) Field of Search ................ 428/216, 36.8; 2/168

(56) References Cited

U.S. PATENT DOCUMENTS

| 4,499,154 | A | 2/1985 | James et al. ............... 428/494 |
| 4,515,851 | A | 5/1985 | Johnson ..................... 428/246 |
| 4,519,098 | A | 5/1985 | Dunmire et al. ........... 2/161 R |
| 4,555,813 | A | 12/1985 | Johnson ..................... 2/161 R |
| 4,589,940 | A | 5/1986 | Johnson ..................... 156/78 |
| 4,920,172 | A | 4/1990 | Daoud ...................... 524/502 |
| 5,088,125 | A | 2/1992 | Ansell et al. ................ 2/167 |
| 5,272,771 | A | 12/1993 | Ansell et al. ................ 2/167 |
| 5,284,607 | A | 2/1994 | Chen ........................ 264/37 |
| 5,368,930 | A | 11/1994 | Samples .................... 428/323 |
| 5,370,900 | A | 12/1994 | Chen ........................ 427/2.3 |
| 5,399,400 | A | 3/1995 | Nile et al. ................. 428/36.8 |
| 5,405,666 | A | 4/1995 | Brindle ..................... 428/36.4 |
| 5,438,709 | A | 8/1995 | Green et al. ................ 2/167 |
| 5,459,880 | A | 10/1995 | Sakaki et al. ............... 2/168 |
| 5,534,350 | A | 7/1996 | Liou ........................ 428/423.1 |
| 5,742,943 | A | * 4/1998 | Chen ........................ 2/168 |
| 5,872,173 | A | * 2/1999 | Anand ...................... 524/494 |
| 5,993,923 | A | * 11/1999 | Lee ......................... 428/36.8 |
| 6,016,570 | A | * 1/2000 | Vande Pol et al. .......... 2/161.7 |
| 6,075,081 | A | * 6/2000 | Nile et al. ................. 524/429 |
| 6,306,514 | B1 | * 10/2001 | Weikel et al. .............. 428/451 |

OTHER PUBLICATIONS

"Antiozonates," pp. 58–59.
"Waxes," pp. 1306–1307.

* cited by examiner

Primary Examiner—Cynthia H. Kelly
Assistant Examiner—L. Ferguson
(74) Attorney, Agent, or Firm—Gardner & Carton & Douglas LLP

(57) ABSTRACT

The invention provides elastomeric articles having a layer of natural or synthetic rubber and at least one layer of a coating containing a blend of a film forming polymer and a wax. A process of making the elastomeric articles is also provided. Examples of elastomeric articles of the invention include surgeons' gloves which have improved lubricity and exhibit enhanced donning properties with respect to dry, damp or wet hands.

16 Claims, 1 Drawing Sheet

ELASOMERIC ARTICLE

BACKGROUND OF THE INVENTION

Figure 1:
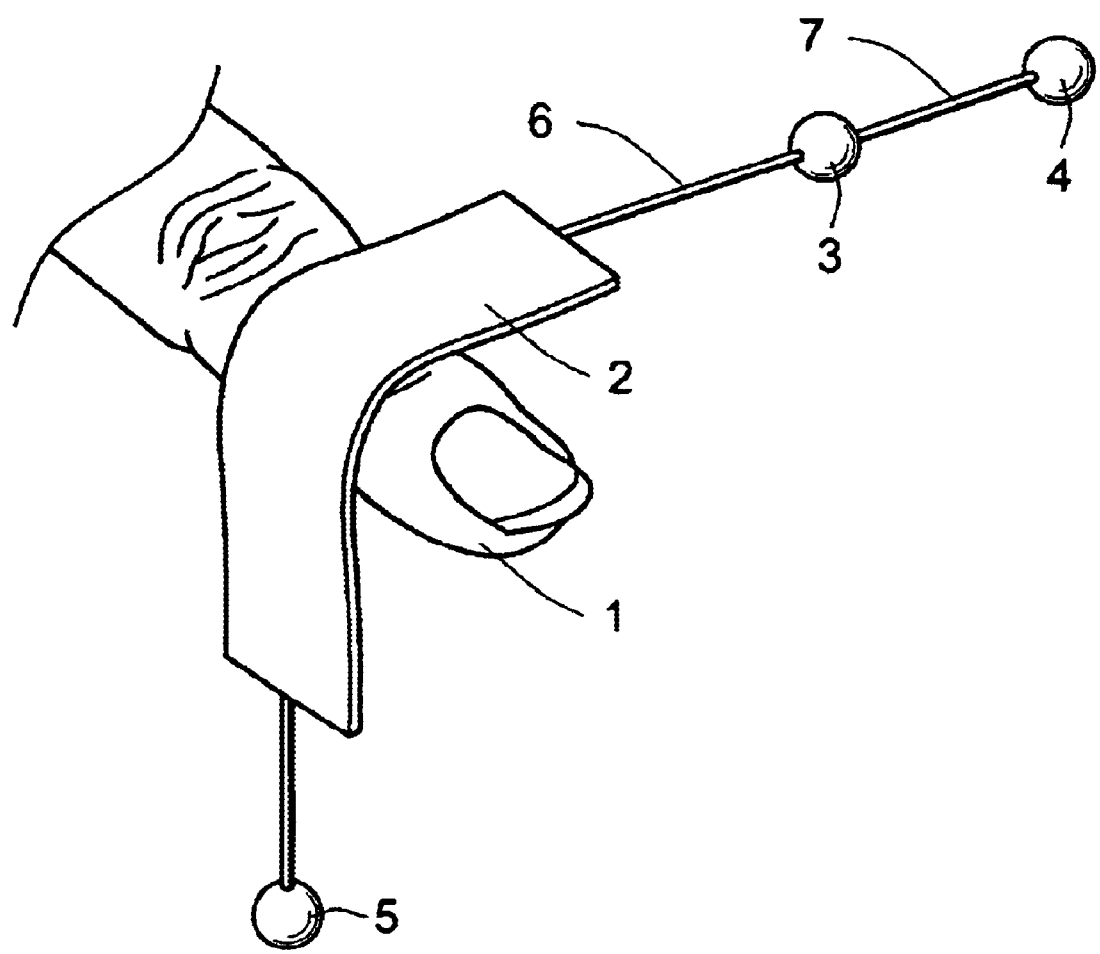

The present invention relates to elastomeric articles which exhibit enhanced lubricity with respect to both dry and damp surfaces and in particular to flexible elastomeric articles such as films and gloves which are powder free and exhibit enhanced lubricity with respect to both dry and damp surfaces such as skin.

Elastomeric articles such as medical gloves are generally required to be tight fitting. This requirement makes donning the gloves difficult unless they are lubricated. It has been common practice to utilise powder lubricants such as modified corn starch or talc applied to the inner surface of medical gloves to facilitate donning. However, certain post-operative complications including adhesions, peritonitis and granuloma formation have been attributed to the use of loose powder as a lubricant on gloves and other items used in surgery.

Much effort has been devoted to developing medical gloves which may be readily donned but which do not utilise a powder lubricant. Approaches which have been tried include depositing a granular material on the inner surface of the gloves, bonding to the outer elastomeric layer an inner layer comprising embedded particles, halogenating the gloves and bonding a lubricating hydrogel polymer to the inner surface of the glove and treating the surface with a surfactant.

Although each of the above approaches has its merits, none provide a medical glove which may be as readily donned as a powdered glove, especially when the hands are damp or wet.

We have now found an elastomeric article comprising a coating which provides the article with enhanced lubricity with respect to both dry and wet or damp surfaces.

SUMMARY OF THE INVENTION

Accordingly, the present invention provides an elastomeric article having a first layer of natural or synthetic rubber and at least one layer of a coating of a polymer blend comprising at least one film forming polymer and at least one wax.

In another aspect, the present invention also provides a process for making an elastomeric article comprising forming a first layer of natural or synthetic rubber followed by coating at least one surface of the first layer with a layer of a polymer blend comprising a film forming polymer and a wax.

DETAILED DESCRIPTION OF THE INVENTION

Preferred elastomeric articles according to the invention are medical gloves and the present invention is described primarily with reference to surgeons' gloves. However, the elastomeric articles of the invention may include other elastomeric articles and particularly elastomeric articles which may have contact with skin or other tissue. Such articles include: films, sheets, examination gloves used by doctors, veterinary practitioners, dentists, nurses and other personnel coming into contact with animals or animal fluids; finger stalls; condoms; catheters, ureters, and sheath type incontinence devices.

Suitable elastomers which may be used for the first or rubber layer of the elastomeric articles of the present invention include natural rubber latex, nitrile rubber latex, polychloroprene, styrene-butadiene rubber or a polyurethane. Preferably the first or rubber layer of the elastomeric article comprises natural latex rubber and more preferably, the first or rubber layer of the elastomeric article comprises natural latex rubber glove.

In the elastomeric article of the present invention, the film forming polymer component of the polymer blend coating may be selected from a range of film forming polymers including acrylic polymers and copolymers, methacrylate polymers and copolymers, polyurethane polymers and carboxylated styrene-butadiene copolymers.

Preferably the film forming polymer of the polymer blend is a polyurethane. Suitable polyurethanes include aliphatic polyurethanes and aromatic polyurethanes. Preferably the polyurethane is used in the form of an aqueous dispersion. Examples of suitable commercially available polyurethanes include, but are not limited to, BEETAFIN™ L9009, Witcobond™ W-506, and Neorez™ R-972.

In the elastomeric article of the present invention, the wax component is preferably a synthetic polymer or copolymer wax and more preferably a polyethylene wax, high density polyethylene wax, an oxidised or modified polyethylene wax or high density polyethylene wax or a mixture of such waxes. Preferably, the wax has a melting point equal to or above 80° C. and more preferably the wax is a polyethylene wax having a melting point equal to or above 80° C. Examples of suitable commercially available polyethylene waxes include, but are not limited to, AQUAMAT™ 213, MICHEM LUBE™ 61335 and AQUACER™ 502.

The polymer blend coating used in the present invention may also comprise conventional additives and modifiers including surfactants, antioxidants, antistatic agents, bactericidal or bacteriostatic agents and hardness modifiers. Suitable bactericidal and/or bacteriostatic agents may be selected from the known group of quaternary amine compounds. Suitable hardness modifiers may be selected from polymeric compounds including, but not limited to, poly(2-hydroxyethylmethacrylate), acrylic polymers and melamine-formaldehyde resins. Preferably, the hardness modifier is a polymer or copolymer having a glass transition temperature (Tg) higher than that of the film forming polymer.

In the elastomeric article of the present invention, the ratio of film forming polymer to wax in the polymer blend is preferably at least 0.5 to 1 and more preferably between 0.5 to 1 and 20 to 1.

Preferably the polymer blend is applied to the first layer of natural or synthetic rubber in the form of an aqueous dispersion or emulsion. For example, the film forming polymer and the wax are dispersed in water in the presence of one or more suitable surfactants. Suitable surfactants may be chosen from a range of commercially available non-ionic and anionic surfactants including for example, those sold under the trade marks DARVAN™ and SYNPERONIC™. Typically the aqueous dispersion of the polymer blend comprises 3 to 30% by weight solids and more preferably 5 to 20% by weight solids. The concentration of the surfactant (s) is preferably 0.01 to 0.10% (w/v), most preferably 0.02 to 0.05% (w/v).

The elastomeric articles of the present invention may be made by forming the first layer of natural or synthetic rubber and then applying to at least one surface of the first layer, a coating of a polymer blend comprising at least one film forming polymer and at least one wax.

Between formation of the first layer and coating with the polymer blend, the first layer of natural or synthetic rubber optionally may be heated until the layer is gelled or the surface of the first layer to be coated may be leached.

Optionally the surface of the first layer which is to be coated with the polymer blend may be treated to improve adhesion between the first layer and the polymer blend. Suitable methods for surface treatment of the first layer may include treatment with an oxidising agent such as an aqueous solution of an alkali metal or alkaline earth metal hypochlorite followed by leaching in water, preferably hot water. Alternatively, the surface of the first layer which is to be coated with the polymer blend may be treated with an agent, such as a dilute aqueous solution of aluminium sulfate or calcium nitrate, to promote deposition of the polymer blend onto the surface of the first layer.

For convenience, the process of the present invention may be illustrated by reference to surgeons' gloves. In such a process a conventional method for preparing latex rubber gloves, such as described in a bulletin "Dipping With Natural Rubber Latex" by the Malaysian Rubber Producers' Research Association, Hertford, England, 1980, is employed. For example, a former coated with a coagulant is first dipped into natural or synthetic latex. After withdrawal, the glove on the former is heated until the film is significantly gelled. The glove may then be subjected to leaching.

The polymer blend may then be applied to the first layer of natural or synthetic rubber by dipping the glove on the former into a bath of an aqueous dispersion and/or solution of the polymer blend.

The first layer of natural or synthetic rubber can be 0.10–0.40 mm, preferably 0.15–0.30 mm. The layer of polymer blend is preferably 1–10 μm, most preferably 2–5 μm.

After application of the polymer blend the glove is then dried and cured. This improves adhesion of the polymer blend coating to the rubber. The curing can be conducted at a temperature which approaches, is similar to, or exceeds, the melting point of the wax used in the polymer blend, so long as it results in bonding of the polymer blend to the rubber base.

The resulting glove may be further treated according to methods known in the art to further improve glove donning and/or to reduce blocking. Such further treatment includes treatment with a silicone by, for example, contacting with an aqueous dispersion or emulsion or solution of a silicone in the presence of a surfactant.

As hereinbefore indicated, the elastomeric articles or the present invention have improved lubricity with respect to dry, wet or damp surfaces. For example, surgeons' gloves according to the present invention show excellent donning properties with respect to dry, damp or wet hands. Moreover, the elastomeric articles of the present invention may be readily manufactured and show enhanced lubricity without the need to use conventional powder lubricants.

FIG. 1 is a diagrammatic representation of the measurement of lubricity of an elastomeric article.

In the measurement of lubricity, a strip of the elastomeric article 15 mm×150 mm (2) is placed between the first and second knuckle of the fore-finger (1) such that the surface to be measured is in contact with the finger. The leading section of the test piece (2) is connected to a load cell (3) which is mounted on a sledge linked to a constant speed driving mechanism (4). The trailing section of the test piece is attached to a three gm load (5). The finger is positioned such that the leading section of the test piece, the length of nylon filament (6), the length of the horizontal sledge and the length of nylon filament (7) are parallel. The test piece is moved around the finger at around a speed of 2.5 mm per second for a distance of approximately 50 mm and the average friction force recorded.

The results obtained utilising this test clearly show that elastomeric articles of the present invention have a significantly higher lubricity than prior art elastomeric articles.

The present invention is now illustrated in greater detail by the following specific examples. It is to be understood that these examples are given by way of illustration and are not to be interpreted as limiting the scope of the claims. All percentages in the examples, and elsewhere in the specification, are by weight unless otherwise specified.

EXAMPLE 1

A surgeons' glove of natural rubber latex was formed by conventional dipping process. Upon withdrawing from the latex bath, the glove on the former was heated until the film was sufficiently gelled. The glove was then leached in hot water, treated with 2% dilute sodium hypochlorite, leached again in hot water and dried out before dipping into a dispersion of a polymer blend, the composition of which is described in Table I.

TABLE I

|  | Parts by Weight |
| --- | --- |
| Film forming polymer (Beetafin PU L9009) | 10 |
| Polyethylene wax (Aquamat 213) | 3 |
| Hardness Modifier (Cymel 373) | 1 |
| Surfactant (Darvan WAQ) | 0.025 |
| Deionized water | 86 |

After curing, the glove was leached and treated with silicone emulsion consisting of 0.05 to 0.25% of silicone and 0.05 to 0.25% of cetyltrimethyl-ammonium chloride. The finished glove shows good dry, damp and wet donning properties and is found to have less than 2 mg of powder mass/glove as measured in accordance with ASTM D 6124-97.

EXAMPLE 2

Example 1 was repeated except that the glove was dipped into a 0.5% solution of aluminium sulphate prior to coating and the glove was not treated with silicone emulsion. Application of alum allows a thicker and more uniform coating to be formed. The coating exhibits good lubricity with respect to dry, damp and wet hands.

EXAMPLE 3

Example 1 was repeated except that the glove was dipped into a 0.5% solution of aluminium sulphate prior to coating. Application of alum allows a thicker and more uniform coating to be formed. The coating exhibits good lubricity with respect to dry, damp and wet hands.

EXAMPLE 4

Example 2 was repeated except that the coating was replaced by the polymer blend indicated in Table II.

TABLE II

| | Parts by Weight |
|---|---|
| Film forming polymer (Witcobond W-506) | 6.2 |
| Polyethylene wax (Michem Lube 61335) | 2.0 |
| Hardness Modifier (Cymel 373) | 0.7 |
| Surfactant (Darvan WAQ) | 0.018 |
| Surfactant (Synperonic NP40) | 0.019 |
| Deionized Water | 91 |

The finished glove shows good dry, damp and wet donning properties and is found to have less than 2 mg of powder mass/glove as measured in accordance with ASTM D 6124-97.

EXAMPLE 5

Example 4 was repeated except that after curing, the glove was leached and treated with silicone emulsion consisting of 0.05 to 0.25% of silicone and 0.05 to 0.25% of cetyltrimethylammonium chloride. The finished glove shows good dry damp and wet donning properties.

EXAMPLE 6

A thin-walled glove of chloroprene latex was formed by conventional dipping process. Upon withdrawal from the latex bath, the glove on the former was heated until it was sufficiently gelled. The glove was then leached in hot water before dipping into a dispersion of a polymer blend, the composition of which is given in Table III.

TABLE III

| | Parts by Weight |
|---|---|
| Film forming polymer (NeoRez R-972) | 10 |
| Polyethylene wax (Aquacer 502) | 3 |
| Hardness Modifier (Cymel 373) | 1 |
| Surfactant (Darvan WAQ) | 0.025 |
| Deionized water | 86 |

After curing, the glove was treated with silicone emulsion comprising 0.05 to 0.25% of silicone and 0.05 to 0.25% of cetyltrimethylammonium chloride. The finished glove shows good dry, damp and wet donning properties.

EXAMPLE 7

The skin lubricity of the elastomeric articles of the present invention was compared with the skin lubricity of prior art elastomeric articles according to the following test.

With reference to FIG. 1 a strip of the elastomeric article 15 mm×150 mm (2) was placed between the first and second knuckle of the forefinger (1) such that the surface to be measured was in contact with the finger. The leading section of the test piece (2) was connected to a load cell (3) which was mounted on a sledge linked to a constant speed driving mechanism (4). The trailing section of the test piece was attached to a 3 gm load (5). The finger was positioned such that the leading section of the test piece, the length of nylon filament (6), the length of the horizontal sledge and the length of nylon filament (7) were parallel. The test piece was moved around the finger at a speed of 2.5 mm/sec for a distance of approximately 50 mm and the average friction force recorded.

A measure of lubricity, hereinafter referred to as "Lubricity Number" was obtained by dividing the dry friction force measured for natural, uncoated, non-powdered rubber (Comparative Example 1) by the friction force measured for each sample. The results, recorded in Table IV, are the averages of nine determinations from three individuals. The higher the Lubricity Number the higher the lubricity.

TABLE IV

| Elastomeric Article[1] | Friction Force (g) | Lubricity Number |
|---|---|---|
| Comparative Example 1[2] | 59.9 | 1.0 |
| Comparative Example 2[3] | 6.2 | 9.7 |
| Comparative Example 3[4] | 23.2 | 2.6 |
| Example 2 | 7.0 | 8.6 |
| Example 3 | 6.3 | 9.5 |
| Comparative Example 4[5] | 12.7 | 4.7 |
| Example 4 | 7.6 | 7.9 |
| Example 5 | 6.3 | 9.5 |

1. Samples taken from formed surgeons' gloves.
2. Natural rubber latex without coating or powder.
3. Natural rubber latex without coating but powdered.
4. Natural rubber latex with polyurethane polymer coating but without polyethylene wax, prepared essentially as described in Example 2.
5. Natural rubber latex with polyurethane polymer coating but without polyethylene wax, prepared essentially as described in Example 4.

It will be understood that the invention disclosed and defined in this specification extends to all alternative combinations of two or more of the individual features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

What is claimed is:

1. An elastomeric article comprising:
   a first layer of natural or synthetic rubber; and
   a second layer, the second layer dipped coating of a polymer blend comprising a film forming polymer and a synthetic wax, wherein
   the synthetic wax is selected from the group consisting of synthetic polymer wax, synthetic copolymer wax, polyethylene wax, high density polyethylene wax, oxidised polyethylene wax, modified polyethylene wax, oxidised high density polyethylene wax, modified high density polyethylene wax, and mixtures thereof.

2. The elastomeric article according to claim 1 wherein the first layer of natural or synthetic rubber is selected from natural rubber latex, nitrile rubber latex, polychloroprene, styrene-butadiene rubber or a polyurethane.

3. The elastomeric article according to claim 1 wherein the film forming polymer is selected from the group consisting of acrylic polymers, methacrylate polymers, polyurethane polymers, carboxylated styrene-butadiene polymers and copolymers thereof.

4. The elastomeric article according to claim 1 wherein the synthetic wax is selected from the group consisting of synthetic polymer wax and synthetic copolymer wax.

5. The elastomeric article according to claim 1 wherein the natural or synthetic rubber includes a natural rubber latex or polychloroprene.

6. The elastomeric article according to claim 1 wherein the film forming polymer includes a polyurethane.

7. The elastomeric article according to claim 1 wherein the synthetic wax is polyethylene wax.

8. The elastomeric article according to claim 7 wherein the synthetic wax is polyethylene wax having a melting point greater than or equal to 80° C.

9. The elastomeric article according to claim 1 wherein the polymer blend further includes a hardness modifier.

10. The elastomeric article according to claim 9 wherein the hardness modifier has a glass transition temperature higher than that of the film forming polymer.

11. The elastomeric article according to claim 9 wherein the hardness modifier is selected from a melamine formaldehyde resin, an acrylic polymer, a poly(2-hydroxyethyl methacrylate) or a mixture thereof.

12. The elastomeric article according to claim 1 wherein the first layer includes natural rubber latex the film forming polymer includes a polyurethane, the synthetic wax includes polyethylene wax and wherein the polymer blend further includes a hardness modifier.

13. The elastomeric article according to claim 1 wherein said article is a surgeons' glove and wherein the first layer is an outer layer and the coating of a polymer blend comprises the inner layer.

14. The elastomeric article according to claim 13, wherein the first layer is 0.10–0.40 mm thick and the coating is 1–10 µm thick.

15. The elastomeric article according to claim 1 further comprising a silicone emulsion.

16. The elastomeric article according to claim 15, wherein the silicone emulsion further includes a surfactant.

\* \* \* \* \*

UNITED STATES PATENT AND TRADEMARK OFFICE
CERTIFICATE OF CORRECTION

PATENT NO. : 6,709,725 B1
DATED : March 23, 2004
INVENTOR(S) : Lai et al.

It is certified that error appears in the above-identified patent and that said Letters Patent is hereby corrected as shown below:

<u>Title page,</u>
Item [54], Title should read -- ELASTOMERIC ARTICLE --

Signed and Sealed this

Twenty-ninth Day of June, 2004

JON W. DUDAS
*Acting Director of the United States Patent and Trademark Office*